(12) United States Patent
Ohtsuka et al.

(10) Patent No.: US 8,497,113 B2
(45) Date of Patent: Jul. 30, 2013

(54) CHLORIDE ION-RESISTANT SULFUR-OXIDIZING BACTERIA

(75) Inventors: Norimasa Ohtsuka, Ibaraki (JP); Tsuyoshi Mitarai, Ibaraki (JP)

(73) Assignee: JX Nippon Mining & Metals Corporation, Tokyo (JP)

( * ) Notice: Subject to any disclaimer, the term of this patent is extended or adjusted under 35 U.S.C. 154(b) by 1617 days.

(21) Appl. No.: 11/651,453

(22) Filed: Jan. 10, 2007

(65) Prior Publication Data

US 2007/0202584 A1 Aug. 30, 2007

(30) Foreign Application Priority Data

Feb. 6, 2006 (JP) .................................. 2006-28675

(51) Int. Cl.
*C12N 1/20* (2006.01)
(52) U.S. Cl.
USPC ...................................... 435/252.1; 424/93.1
(58) Field of Classification Search
None
See application file for complete search history.

(56) References Cited

U.S. PATENT DOCUMENTS 3,347,661 A 10/1967 Mayling et al.

FOREIGN PATENT DOCUMENTS

| CA | 2269301 A1 | 10/2000 |
| WO | WO-02/081761 A2 | 10/2002 |

OTHER PUBLICATIONS

Smith et al., Arch Microbial (1981) 129: 199-203.*
Kamimura et al., Extremophiles, 2005, vol. 9 pp. 45-51.
Kamimura et. al., Extremophiles, 2003, vol. 7, pp. 95-99.
Harahuc et al., "Selective Inhibition of the Oxidation of Ferrous Iron or Sulfur in *Thiobacillus ferrooxidans*," Applied and Environmental Microbiology, Mar. 2000, pp. 1031-1037.
Kelly et al., "Reclassification of some species of *Thiobacillus* to the newly designated genera *Acidithiobacillus* gen. nov., *Halothiobacillus* gen. nov. and *Thermithiobacillus* gen. nov.," International Journal of Systematic and Evolutionary Microbiology, 2000, vol. 50, pp. 511-516.

* cited by examiner

*Primary Examiner* — Irene Marx
(74) *Attorney, Agent, or Firm* — Birch, Stewart, Kolasch & Birch, LLP

(57) ABSTRACT

A microorganism having an ability to oxidize sulfur even at high chloride ion concentration is provided. Specifically, a microorganism belonging to the genus *Acidithiobacillus* having the ability to oxidize sulfur even at high chloride ion concentration is provided. A method for bacterial leaching of copper sulfide ores and a method for improving alkaline soil using the microorganism are also provided.

1 Claim, 4 Drawing Sheets

SEQUENCE LISTING

```
<160> NUMBER OF SEQ ID NOS: 3

<210> SEQ ID NO 1
<211> LENGTH: 909
<212> TYPE: DNA
<213> ORGANISM: Acidithiobacillus sp.

<400> SEQUENCE: 1
gggcgcgtag gcggtgggtt acgtctgccg tgaaatcccc gggctcaacc tgggaatggc      60
ggtggaaacg ggctgactag agtatgggag agggtgatgg aattccaggt gtagcggtga     120
aatgcgtaga gatctggagg aacatcagtg gcgaaggcgg tcacctggcc caatactgac     180
gctgaggcgc gaaagcgtgg ggagcaaaca ggattagata ccctggtagt ccacgcccta     240
aacgatggat actagatgtt tggtgcctta ggtgctgagt gtcgtagcta acgtgataag     300
tatcccgcct gggaagtacg gccgcaaggt taaaactcaa aggaattgac ggggccccgc     360
acaagcggtg gagcatgtgg tttaattcga tgcaacgcgc agaaccttac ctgggcttga     420
catccagaga atcctgcaga gatgtgggag tgccttcggg aactctgaga caggtgctgc     480
atggctgtcg tcagctcgtg tcgtgagatg ttgggttaag tcccgcaacg agcgcaaccc     540
ttgtccctag ttgccagcgg ttcggccggg cactctaggg agactgccgg tgacaaaccg     600
gaggaaggtg gggatgacgt caagtcctca tggcctttat gtccagggct acacacgtgc     660
tacaatggcg cgtacagagg gaagcgagac cgcgaggtgg agcagacccc agaaagcgcg     720
ccgtagttcg gattgcagtc tgcaactcga ctgcatgaag tcggaatcgc tagtaatcgc     780
ggatcagcat gccgcggtga atacgttccc gggccttgta cacaccgccc gtcacaccat     840
gggagtggat tgtaccagaa gcagctagcc taaccttcgg ggggcggtt accacggtat     900 ggttcatga                                                              909

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
cgtgccagca gccgcggtaa t                                                 21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: synthetic
      DNA
```

-continued

```
<400> SEQUENCE: 3
aaggaggtga tccagccgca                                              20
```

CHLORIDE ION-RESISTANT SULFUR-OXIDIZING BACTERIA

TECHNICAL FIELD

The present invention relates to microorganisms that gain energy and grow by oxidizing sulfur substances to sulfuric acid without inactivation of the ability to oxidize sulfur even at high chloride ion concentration and use thereof.

BACKGROUND ART

Sulfur-oxidizing bacteria are gram-negative autotrophic bacteria and gain energy to grow by oxidizing sulfur substances to sulfuric acid. Taking advantage of this characteristic, application of sulfur-oxidizing bacteria to industrial fields typically includes bacterial leaching to recover copper by leaching it from copper sulfide ores ("Biseibutsu Shigenkougaku" (in Japanese) written and edited by Tadashi Chida (1996), Corona Publishing Co., Ltd. (Tokyo), pp. 74-83) and improvement of alkaline soil (JP Patent Publication (Kokai) No. 11-319795A (1999)). However, there is a problem that the ability of sulfur-oxidizing bacteria to oxidize sulfur is markedly inhibited at high chloride ion concentration because of influence of osmotic pressure and toxicity of chloride ion.

DISCLOSURE OF THE INVENTION

Thus, an object of the present invention is to provide microorganisms having an excellent ability to oxidize sulfur even at high chloride ion concentration.

As a result of intensive studies to solve the above-mentioned problems, the present inventors discovered a microorganism having an ability to oxidize sulfur even at high chloride ion concentration among microorganisms belonging to the genus *Acidithiobacillus* and perfected the present invention.

That is, the present invention encompasses the following inventions:

(1) A microorganism belonging to the genus *Acidithiobacillus* having an ability to oxidize sulfur even at high chloride ion concentration.
(2) The microorganism according to (1) in which the microorganism belonging to the genus, *Acidithiobacillus* is an *Acidithiobacillus* species, TTH-19A strain (NITE BP-164).
(3) A method of leaching copper in which a sulfuric acid solution containing the microorganism according to (1) or (2) is allowed to act on copper sulfide ores at high chloride ion concentration to leach copper from the copper sulfide ores into the solution.
(4) A method of improving alkaline soil in which the microorganism according to (1) or (2) and a sulfur source are applied to alkaline soil.

Figure 1:
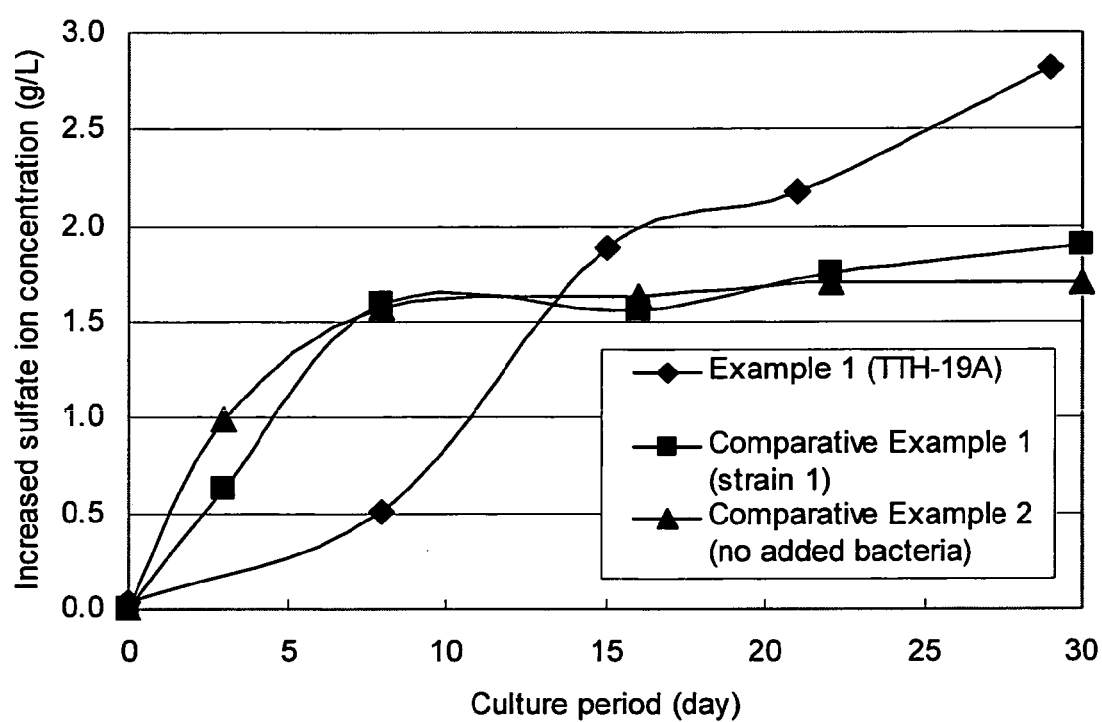
FIG. 1 is a graph showing time course changes in increased sulfate ion concentration in cultured medium when sulfur-oxidizing bacteria were cultured using a culture medium (with chalcopyrite as sulfur source) in Example 1 and Comparative Examples 1 and 2 (Example 1, *Acidithiobacillus* sp. TTH-19A strain; Comparative Example 1, *Acidithiobacillus thiooxidans* (strain 1); Comparative Example 2, no added bacteria: sodium chloride concentration of 10 g/L in each case)

Hereinafter the present invention will be described in detail. The present application claims the priority of Japanese Patent Application No. 2006-028675 filed on Feb. 6, 2006 and encompasses contents described in the specification and/or drawings of the patent application.

1. Chloride Ion-Resistant Sulfur-Oxidizing Bacteria

According to the present invention, a microorganism having an ability to oxidize sulfur even at high chloride ion concentration is provided.

In the present specification, "high chloride ion concentration" refers to 5 to 30 g/L, preferably 5 to 20 g/L, as converted into sodium chloride concentration.

An example of such microorganisms can include a TTH-19A strain that was isolated from a soil sample collected at Toyoha mine, Sapporo, Hokkaido, Japan by the present inventors.

Bacteriological characteristics of the TTH-19A strain are as follows:

(a) Morphological characters
Shape and size: rod, 2.0×0.4 μm
Polymorphism: no
Motility: yes
State of adherence of flagella: uncertain
Formation of spores: no
(b) Cultural characters
Broth agar plate culture: no growth
Broth liquid culture: no growth
Broth gelatin stab culture: no growth
Other media containing sugars: no growth
9K medium containing elemental sulfur and no iron: good growth
9K medium containing tetrathionate and no iron: good growth 9K ferrous sulfate medium: no growth
(c) Physiological characters
Gram stain: negative
Range of growth (temperature): 20 to 35 degrees C.; optimal temperature, 30 degrees C.
Range of growth (pH): 1.0 to 4.0
Behavior toward oxygen: aerobic
(d) Other characters
Chloride ion resistance: yes (NaCl concentration range for growth is 0 to 30 g/L but not auxotrophic.)
In addition, DNA extracted from the TTH-19A was amplified by PCR using primers for amplification of bacterial 16S rDNA below,

```
514F:    5' CGTGCCAGCAGCCGCGGTAAT 3'   (SEQ ID NO: 2)

1540R:   5' AAGGAGGTGATCCAGCCGCA 3'    (SEQ ID NO: 3)
``` and the nucleotide sequence of DNA encoding 16S rRNA (hereinafter, referred to as "16S rRNA gene") was determined (SEQ ID NO:1 in Sequence Listing). When homology analysis was performed for partial nucleotide sequences of the 16S rRNA gene from this TTH-19A strain using the GenBank database, the 16S rRNA gene from the TTH-19A strain showed high homology to that from the genus *Acidithiobacillus*.

When the above bacteriological characteristics were compared with reference to the most recent literature on the bacterial taxonomy (International Journal of Systematic and Evolutionary Microbiology, 2000, 50, 511-516), characters other than chloride ion resistance were in accord with those of *Acidithiobacillus thiooxidans*. However, the TTH-19A strain had a character to grow even in the presence of 20 g/L of sodium chloride and its partial nucleotide sequence of the 16S rRNA gene showed only 95.5% homology to that of the type culture of *Acidithiobacillus thiooxidans*, ATCC 19377 strain. From these facts, the TTH-19A strain was named *Acidithiobacillus* sp. TTH-19A strain. This bacterial strain has been deposited under accession number NITE P-164 at the Patent Microorganisms Depositary, National Institute of Technology and Evaluation (NPMD) (2-5-8 Kazusakamatari, Kisarazu-shi, Chiba), an Independent Administrative Institution, since the date of Jan. 13, 2006, and has been transferred to the international deposit on Oct. 20, 2006 as accession No. NITE BP-164 under the terms of the Budapest Treaty.

The microorganism of the present invention also includes, in addition to the TTH-19A strain, microorganisms having specified similarity to this strain (related microorganisms). The microorganisms related to the TTH-19A strain mean, for example, microorganisms having a similarity in the 16S rRNA gene used in bacterial taxonomy to the above strain as well as an ability to oxidize sulfur even at high chloride ion concentration. Specifically, the related microorganisms mean microorganisms having 95% or more homology in the nucleotide sequence of their 16S rRNA genes to that of SEQ ID NO:1, preferably 98% or more homology, further preferably 99% or more homology, as well as an ability to oxidize sulfur even at high chloride ion concentration.

These microorganisms related to the TTH-19A strain can be isolated, for example, from a sample such as acid sulfate soil using the ability to oxidize sulfur at high chloride ion concentration and the nucleotide sequence listed in SEQ ID NO:1 as indexes.

2. Use of the Microorganism of the Present Invention

The microorganism of the present invention has an ability to oxidize sulfur even at high chloride ion concentration. Accordingly, the microorganism of the present invention can be used in a reaction process to oxidize sulfur in a water system (underground water, waste water, seawater, river water, lake water, etc.) and soil containing chloride ion at high concentration and produce sulfuric acid. Use of the microorganism is not particularly limited to any specific form, and either bacterial cells or a treated matter thereof may be accepted. The treated matter of bacterial cells refers to, for example, disrupted bacterial cells, cultures (cultured cells, culture supernatant), and enzymes extracted from the cultures. In addition, the bacterial cells or the treated matter thereof may also be used after immobilization. Examples of the method for immobilization include conventionally known carrier-linkage method, cross-linkage method, and entrapment method. Further, a preparation in which the microorganism is converted to lyophilized dry powder and then the dry powder and inorganic salts to support growth are mixed and granulated to a solid form for easy use (powder, granule, pellet, etc.) may also be used.

The microorganism of the present invention can be suitably used in hydrometallurgy of copper sulfide ores where a sulfuric acid solution, preferably a sulfuric acid solution of high chloride ion concentration, is used as a leaching solution. Further, when it comes to hydrometallurgy of copper using a sulfuric acid solution as the leaching solution, the microorganism of the present invention can be used in any types of leaching operations. For example, not only agitated batch leaching but also pile leaching such as heap leaching and dump leaching where copper is leached into sulfuric acid by sprinkling sulfuric acid over piled ores may be optionally adopted. In addition, pH of the sulfuric acid solution is preferably from 1.4 to 1.8.

Dissolution and leaching of copper sulfide ores proceed through a series of reactions shown in Equation 1 to Equation 3 below.

$$Cu^{2+}+Fe^{2+} \leftrightarrow Cu^{+}+Fe^{3+} \tag{Equation 1}$$

$$CuFeS_2+Cu^{+}+Fe^{3+} \rightarrow Cu_2S+2Fe^{2+}+S \tag{Equation 2}$$

$$Cu_2S+4Fe^{3+} \rightarrow 2Cu^{2+}+4Fe^{2+}+S \tag{Equation 3}$$

Further, elemental sulfur produced in the reactions shown in the above Equation 2 and Equation 3 is oxidized to sulfuric acid by an action of sulfur-oxidizing bacteria in a leaching solution according to a reaction shown in Equation 4 below.

$$S+1.5O_2+H_2O \rightarrow H_2SO_4 \tag{Equation 4}$$

Since the equilibrium of the above Equation 1 is shifted toward the right by increasing chloride ion concentration in the leaching solution, the reactions in Equation 2 and subsequent Equation 3 can be accelerated as the result, which is advantageous for acceleration of copper leaching rate. The ability of the microorganism of the present invention to oxidize sulfur (sulfur-oxidizing bacteria) is not reduced even at high chloride ion concentration; therefore the reaction in Equation 4 proceeds smoothly even when a leaching solution of high chloride ion concentration is used. As the result, attachment of elemental sulfur produced by the leaching reactions to ore surfaces does not occur, thereby enabling efficient copper leaching.

Although the amount of the microorganism of the present invention added to a leaching solution is not particularly limited, it is generally added so that the bacterial density becomes $1 \times 10^6$ to $1 \times 10^7$ cells/mL. The bacterial density varying with time is not necessary to be specifically adjusted.

Further, the microorganism of the present invention makes it possible to improve alkaline soil in areas of high chloride ion concentration such as areas near coast and areas polluted with domestic wastewater and industrial wastewater containing a large amount of salts.

When the microorganism of the present invention is used for improvement of alkaline soil, the microorganism of the present invention (bacterial cells and a treated matter thereof) is applied to alkaline soil with a sulfur source (sulfur, sulfur compounds), thereby making it possible to decrease pH of the alkaline soil with sulfuric acid produced by sulfur oxidation of the microorganism. As the sulfur, a solution of sulfur powder (iron and steel slag leachate, etc.) and as the sulfur compound, pyrite, sodium thiosulfate, and the like are used. The application may be carried out by a method commonly employed in the field, and examples of the method include a method in which the microorganism and a sulfur source are directly sprinkled over soil and mixed and a method in which a liquid composition containing cultured medium of the microorganism and a sulfur source is poured or injected under pressure from a well or pipe placed underground. At the time of the application, water and air (oxygen) are appropriately supplied.

Although the amount of the microorganism of the present invention to be used for alkaline soil can be arbitrarily set depending on application mode, generally ca. 1 L of cultured medium or ca. 5 g of dry bacterial cells per 1 m$^2$ soil is exemplified.

BEST MODES FOR CARRYING OUT THE INVENTION

Hereinafter, the present invention is more specifically explained by way of examples and comparative examples. However, the present invention is not limited thereto.

EXAMPLE 1

Concentrate of Chilean origin containing chalcopyrite as a main constituent was used as a target sulfur substance. This quality was as follows: Cu, 28% by mass; Fe, 28% by mass; S, 32% by mass.

Three gram of the above concentrate was mixed with 300 mL of a culture medium (containing ammonium sulfate 3 g/L, potassium hydrogenphosphate 0.5 g/L, magnesium sulfate heptahydrate 0.5 g/L, and potassium chloride 0.1 g/L) adjusted to pH 1.5 to 1.8 with sulfuric acid and poured into a 500 mL Shaking flask. To the culture medium in the flask, sodium chloride was added so that the concentration became 10 g/L, and further the sulfur-oxidizing bacterium, *Acidithiobacillus* sp. TTH-19A, was added at a density of 1×10$^7$ cells/mL. Then the flask was plugged with a sponge stopper and shaken at room temperature. The concentration of sulfate ion in the cultured medium was measured with time using an ICP emission spectrophotometer. The bacterial density of the culture was also measured with time using a Thoma hemocytometer under a phase contrast optical microscope.

COMPARATIVE EXAMPLES 1 AND 2

Cultures were shaken at room temperature as in Example 1 except that an *Acidithiobacillus thiooxidans* (strain 1) non-resistant to chloride ion was added to the culture medium prepared in Example 1 at a cell density of 1×10$^7$ cells/mL (Comparative Example 1) or that no sulfur-oxidizing bacterium was added (Comparative Example 2), and likewise the concentration of sulfate ion and bacterial density of the culture were measured with time.

Figure 2:
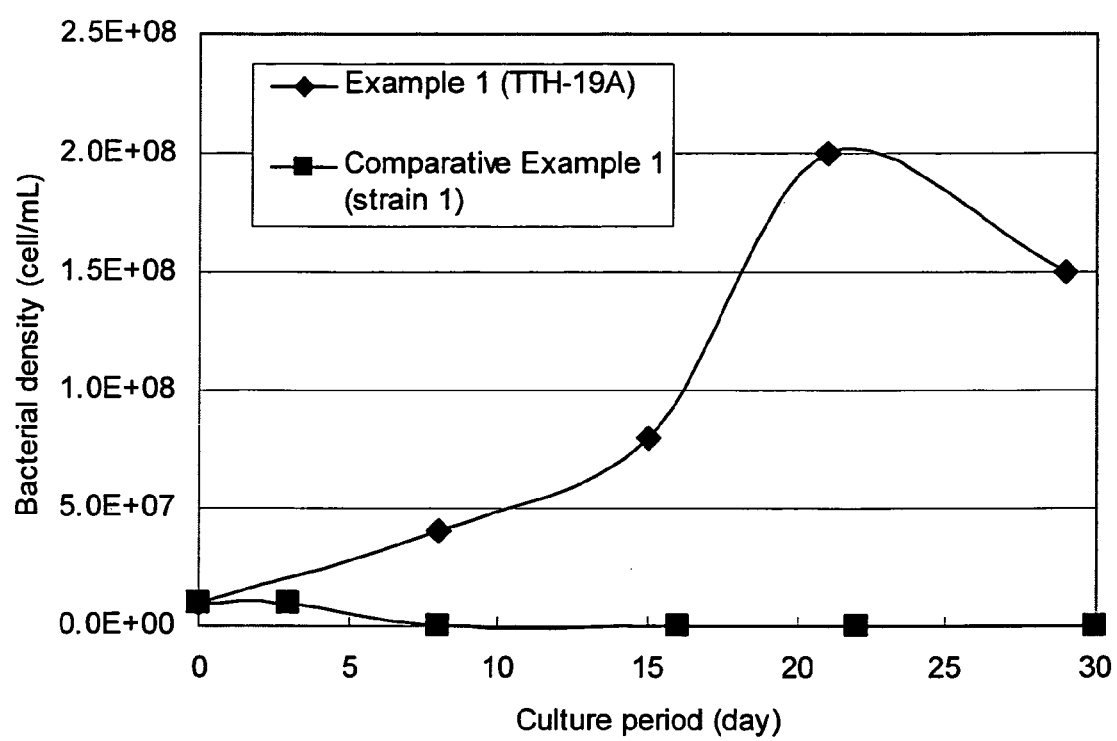
FIG. 2 is a graph showing time course changes in increased bacterial density in cultured medium when sulfur-oxidizing bacteria were cultured using the culture medium (with chalcopyrite as sulfur source) in Example 1 and Comparative Example 1 (Example 1, *Acidithiobacillus* sp. TTH-19A strain; Comparative Example 1, *Acidithiobacillus thiooxidans* (strain 1): sodium chloride concentration of 10 g/L in each case)

The experimental results of Example 1 and Comparative Examples 1 and 2 are shown in FIG. 1 (Changes in increased sulfate ion concentration) and FIG. 2 (Changes in bacterial density).

These results indicated that when culture was carried out using as a sulfur source the copper concentrate containing chalcopyrite as the main constituent under the condition of sodium chloride concentration of 10 g/L, the *Acidithiobacillus* sp. TTH-19A strain grew vigorously by oxidizing the sulfur content. In contrast, in the case of the bacterial strain 1 in Comparative Example 1, an increase in sulfate ion likely due to dissolution of readily soluble sulfate was initially confirmed as in the case of no added bacteria in Comparative Example 2. However, increase in sulfate ion caused by an effect of bacterial oxidation of sulfur content was hardly detected, nor did the bacteria grow.

EXAMPLES 2 AND 3

Elemental sulfur powder (product of Wako Pure Chemical Industries, Ltd., special grade) was used as a target sulfur substance.

One gram of the above sulfur powder was mixed with 300 mL of the culture medium (containing ammonium sulfate 3 g/L, potassium hydrogenphosphate 0.5 g/L, magnesium sulfate heptahydrate 0.5 g/L, and potassium chloride 0.1 g/L) adjusted to pH 1.8 with sulfuric acid and poured into a 500 mL Shaking flask. To the culture medium in the flask, sodium chloride was added so that the concentration became 10 g/L (Example 2) or 20 g/L (Example 3). Further, the sulfur-oxidizing bacterium, *Acidithiobacillus* sp. TTH-19A, was added to the culture medium at a density of 1×10$^6$ cells/mL, and the flask was plugged with a sponge stopper and shaken at room temperature. The concentration of sulfate ion in the cultured medium was measured with time using the ICP emission spectrophotometer.

COMPARATIVE EXAMPLE 3

To the culture medium prepared as in Example 2, no sodium chloride was added, and the sulfur-oxidizing bacterium, *Acidithiobacillus* sp. TTH-19A, was added at a density of 1×10$^6$ cells/mL and shaken at room temperature as above. The concentration of sulfate ion in the cultured medium was measured with time.

COMPARATIVE EXAMPLES 4 TO 6

To the culture medium prepared as in Example 2, no sodium chloride was added (Comparative Example 4), or sodium chloride was added so that the concentration became 10 g/L (Comparative Example 5) and 20 g/L (Comparative Example 6). Further, an *Acidithiobacillus thiooxidans* (strain 2) non-resistant to chloride ion was added to these culture media at a density of 1×10$^6$ cells/mL and shaken at room temperature as above, and the concentration of sulfate ion in the cultured media was measured with time.

Figure 3:
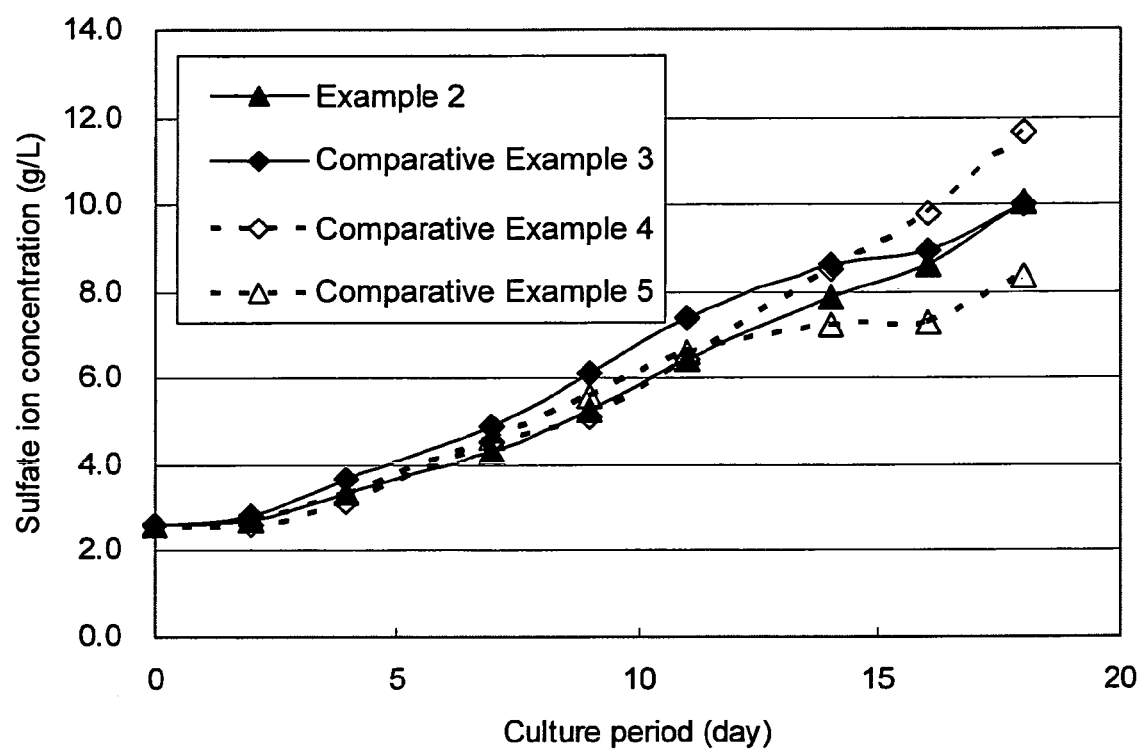
FIG. 3 is a graph showing time course changes in sulfate ion concentration in cultured medium when sulfur-oxidizing bacteria were cultured using a culture medium (with elemental sulfur powder as sulfur source) in Example 2 and Comparative Examples 3 to 5 (Example 2, *Acidithiobacillus* sp. TTH-19A strain and sodium chloride concentration of 10 g/L; Comparative Example 3, *Acidithiobacillus* sp. TTH-19A strain and sodium chloride concentration of 0 g/L; Comparative Example 4, *Acidithiobacillus thiooxidans* (strain 2) and sodium chloride concentration of 0 g/L; Comparative Example 5, *Acidithiobacillus thiooxidans* (strain 2) and sodium chloride concentration of 10 g/L)
Figure 4:
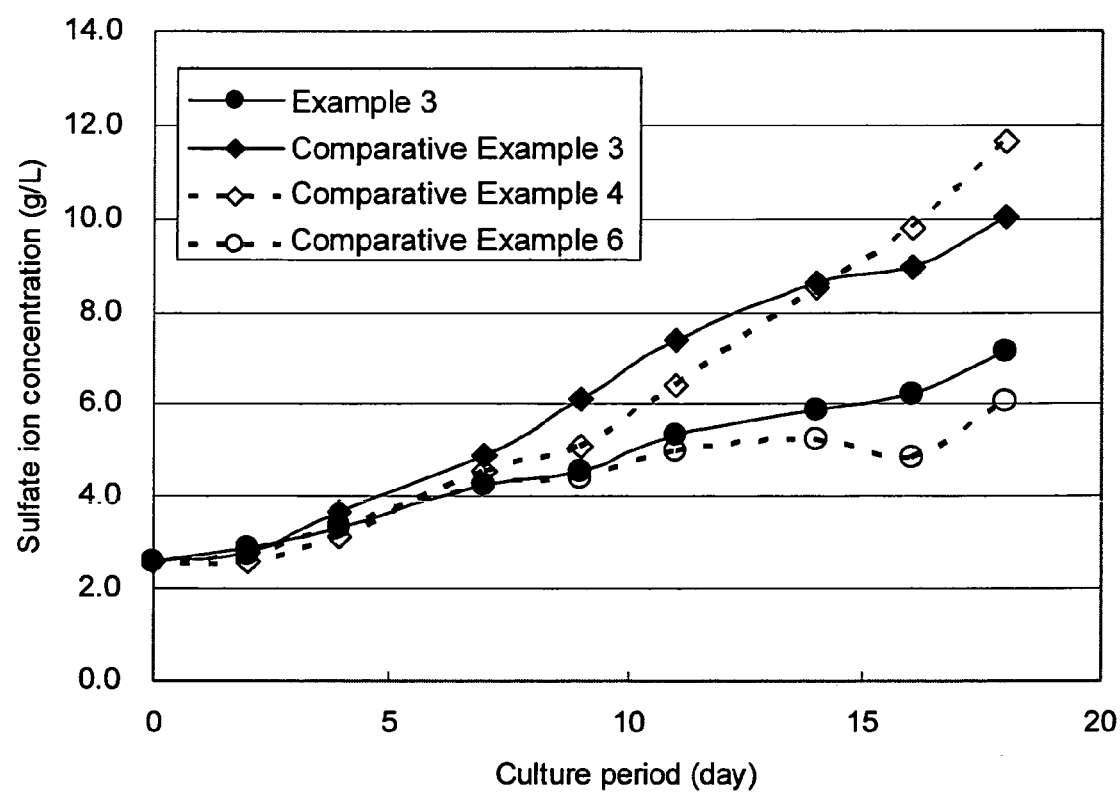
FIG. 4 is a graph showing time course changes in sulfate ion concentration in cultured medium when sulfur-oxidizing bacteria were cultured using the culture medium (with elemental sulfur powder as sulfur source) in Example 3 and Comparative Examples 3, 4, and 6 (Example 3, *Acidithiobacillus* sp. TTH-19A strain and sodium chloride concentration of 20 g/L; Comparative Example 3, *Acidithiobacillus* sp. TTH-19A strain and sodium chloride concentration of 0 g/L; Comparative Example 4, *Acidithiobacillus thiooxidans* (strain 2) and sodium chloride concentration of 0 g/L; Comparative Example 4, *Acidithiobacillus thiooxidans* (strain 2) and sodium chloride concentration of 0 g/L; Comparative Example 6, *Acidithiobacillus thiooxidans* (strain 2) and sodium chloride concentration of 20 g/L).

The experimental results of Examples 2 and 3 and Comparative Examples 3 to 6 are shown in FIGS. 3 and 4.

As shown in FIG. 3, under the condition of sodium chloride concentration of 10 g/L, the *Acidithiobacillus* sp. TTH-19A showed the ability to oxidize sulfur comparable to that when no sodium chloride was added, and inhibition of the ability to oxidize sulfur by chloride ion was not found (comparison between results of Example 2 and Comparative Example 3). On the other hand, inhibition of the ability to oxidize sulfur by chloride ion was found in the strain 2 (comparison between results of Comparative Example 4 and Comparative Example 5).

Further, as shown in FIG. 4, under the condition of sodium chloride concentration of 20 g/L, the ability of the *Acidithiobacillus* sp. TTH-19A to oxidize sulfur was inhibited (comparison between results of Example 3 and Comparative Example 3), but the degree of inhibition of the ability to oxidize sulfur by chloride ion was greater in the strain 2 than in the *Acidithiobacillus* sp. TTH-19A (comparison between results of Comparative Example 4 and Comparative Example 6), resulting in showing a better ability to oxidize sulfur in the *Acidithiobacillus* sp. TTH-19A.

All publications, patents, and patent applications cited herein are incorporated herein by reference in their entirety.

Industrial Applicability

According to the present invention, a microorganism having an ability to oxidize sulfur even at high chloride ion concentration is provided. Accordingly, the present microorganism is capable of efficiently performing bacterial leaching of copper sulfide ores with a leaching solution of high chloride ion concentration.

What is claimed is:
1. A biologically pure culture of *Acidithiobacillus* sp. TTH-19A strain (NITE BP-164) having an ability to oxidize sulfur even at high chloride ion concentrations ranging from 5 to 30 g/l.

* * * * *